(12) United States Patent
Dhal et al.

(10) Patent No.: US 6,294,163 B1
(45) Date of Patent: Sep. 25, 2001

(54) POLYMERS CONTAINING GUANIDINIUM GROUPS AS BILE ACID SEQUESTRANTS

(75) Inventors: Pradeep K. Dhal, Acton; Stephen R. Holmes-Farley, Arlington; John S. Petersen, Acton, all of MA (US)

(73) Assignee: GelTex Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 09/165,386

(22) Filed: Oct. 2, 1998

(51) Int. Cl.[7] ......................... A61K 31/785; A01N 33/18
(52) U.S. Cl. ...................... 424/78.01; 424/78.08; 424/78.17; 424/78.12; 424/78.18; 424/78.19; 424/78.32
(58) Field of Search ................ 424/78.08, 78.17, 424/78.18, 78.19, 78.01, 78.12

(56) References Cited

U.S. PATENT DOCUMENTS

| | | | |
|---|---|---|---|
| 3,856,715 | 12/1974 | Corte et al. | 260/2.1 R |
| 3,878,170 | 4/1975 | Panzer et al. | 260/64 |
| 3,879,258 | 4/1975 | Panzer et al. | 162/166 |
| 3,984,537 | 10/1976 | Harrison et al. | 424/54 |
| 4,253,971 | 3/1981 | MacLeod et al. | 210/759 |
| 4,266,044 | 5/1981 | Timmerman et al. | 525/336 |
| 4,758,595 | 7/1988 | Ogunbiyi et al. | 514/635 |
| 4,836,986 | 6/1989 | Ogunbiyi et al. | 422/28 |
| 4,891,423 | 1/1990 | Stockel | 528/422 |
| 4,946,672 | 8/1990 | Gibbs | 424/76.1 |
| 4,954,636 | 9/1990 | Merianos et al. | 548/519 |
| 5,260,385 | 11/1993 | Iio | 525/328.2 |
| 5,423,990 | 6/1995 | Michiels et al. | 210/669 |
| 5,444,127 | 8/1995 | Miskel, Jr. et al. | 525/504 |
| 5,462,728 | 10/1995 | Blank et al. | 424/49 |
| 5,496,545 | 3/1996 | Holmes-Farley et al. | 424/78.11 |
| 5,607,669 | 3/1997 | Mandeville, III et al. | 424/78.12 |
| 5,618,530 | 4/1997 | Mandeville, III et al. | 424/78.12 |
| 5,624,963 | 4/1997 | Mandeville, III et al. | 514/789 |
| 5,633,344 | * 5/1997 | Figuly | 424/78.01 |
| 5,667,775 | 9/1997 | Holmes-Farley et al. | 424/78.11 |
| 5,679,717 | 10/1997 | Mandeville, III et al. | 514/742 |
| 5,693,675 | 12/1997 | Mandeville, III et al. | 514/742 |
| 5,698,190 | 12/1997 | Hider et al. | 424/78.08 |
| 5,703,188 | 12/1997 | Mandeville, III et al. | 526/290 |
| 5,726,253 | 3/1998 | La Perchec et al. | 525/359.1 |
| 5,741,886 | 4/1998 | Stockel et al. | 528/422 |

FOREIGN PATENT DOCUMENTS

| | | |
|---|---|---|
| 0 460 385 A2 | 12/1991 | (EP) . |
| WO 97/21740 | 6/1997 | (WO) . |
| WO 98/56252 | 12/1998 | (WO) . |

* cited by examiner

*Primary Examiner*—Peter F. Kulkosky
(74) *Attorney, Agent, or Firm*—Hamilton, Brook, Smith & Reynolds, P.C.

(57) ABSTRACT

The present invention relates to a method for sequestering bile acids in a patient and to particular polymers for use in the method. The method comprises administering a therapeutically effective amount of a guanidinium moiety-containing polymer composition to a mammal, such as a human, whereby bile acids are sequestered.

The polymers of the invention comprise guanidinium moieties and optionally, additional substituents such as a hydrophobic group, a quaternary ammonium-containing group or a combination thereof.

32 Claims, No Drawings

POLYMERS CONTAINING GUANIDINIUM GROUPS AS BILE ACID SEQUESTRANTS

BACKGROUND OF THE INVENTION

Biologically, cholesterol is eliminated from the body by conversion into bile acids and excretion as neutral steroids. Bile acids are synthesized from cholesterol in the liver and enter the bile as glycine and taurine conjugates. They are released in salt form in bile during digestion and act as detergents to solubilize and consequently aid in the digestion of dietary fats. Following digestion, bile acid salts are mostly reabsorbed by active transport in the ileum, complexed with proteins, and returned to the liver through hepatic portal veins. The small amount of bile acid salts not reabsorbed in the ileum is excreted via the distal ileum and large intestine, as a portion of the fecal material.

Therefore, reabsorption of bile acids, which can be present as the corresponding salts or conjugates, from the intestine conserves lipoprotein cholesterol in the bloodstream. As such, reducing reabsorption of bile acids within the intestinal tract can lower levels of bile acids circulating in the enterohepatic system thereby promoting replacement of bile acids through de novo synthesis from cholesterol, in the liver. The result is a lowering of circulating blood cholesterol levels.

One method of reducing the quantity of bile acids that are reabsorbed is the oral administration of compounds that sequester the bile acids within the intestinal tract and cannot themselves be absorbed. The sequestered bile acids consequently are excreted.

A need exists for sequestrants that bind bile acid salts and conjugates.

SUMMARY OF THE INVENTION

The present invention relates to a polymer composition comprising polymers containing a guanidinium moiety and to a method of using the guanidinium moiety-containing polymers for sequestering bile acids in a patient.

In one aspect, the guanidinium moiety is found within the backbone of the polymer. In this aspect, the polymer backbone comprises at least two atoms of the guanidinium group. In another aspect, the guanidinium moiety-containing polymer compositions comprise polymers with guanidinium substituents which are pendant from the backbone. For example, the polymer can comprise an aliphatic backbone bearing pendant guanidinium groups which can be further substituted.

In a particular embodiment, the pendant guanidinium substituent is a guanidinium derivative, for example, a cyclic structure wherein the imine nitrogen and the amine nitrogen of a guanidinium group are bonded by a $C_2$–$C_7$ hydrocarbyl chain.

In another embodiment, the pendant guanidinium substituent can have a terminal nitrogen atom of the guanidinium group contained within the backbone of the polymer.

The polymer compositions comprising polymers with pendant guanidinium substituents can be prepared by reacting amine-containing polymers with guanylating agents, as described herein, thereby converting amines of said amine-containing polymers into guanidinium moieties.

In preferred embodiments, the guanidinium moiety-containing polymers can contain additional substituents which are bonded to available amine nitrogen atoms of said polymers. Amine nitrogen atoms which are available for substitution include the nitrogen atoms of primary, secondary or tertiary amines. These substituents can include a hydrophobic group such as a normal or branched alkyl group of at least about four carbon atoms, a quaternary ammonium-containing group such as an alkyltrialkyl ammonium group or combinations thereof. It is to be understood that the guanidinium group, the hydrophobic group and the quaternary ammonium-containing group when employed in any combination can be bonded to the same and/or different amine nitrogen atoms of the polymer.

Optionally the guanidinium moiety-containing polymers are crosslinked. Crosslinking is achieved by the incorporation of a multifunctional co-monomer into the polymer chains, or by means of a multifunctional crosslinking agent.

The method provided by the present invention comprises orally administering to a mammal a therapeutically effective amount of a guanidinium moiety-containing polymer composition, whereby, bile acids are sequestered and consequently excreted. The method of bile acid sequestration provided by the invention is useful to reduce the levels of circulating cholesterol, to treat atherosclerosis and/or to treat hypercholesterolemia. The method includes the administration of polymer compositions of the invention alone or in combination with one or more other antihyperlipoproteineimic or cholesterol lowering agents.

This invention provides many advantages over certain known bile acid sequestrants such as polyammonium salts which sequester bile acid salts through electrostatic interaction between the ammonium cations and the carboxylate and sulfonate anions of the bile acid salts. Guanidinium moiety-containing polymer compositions comprise guanidinium ions which are strong resonance-stabilized cations which remain charged and bind bile acid salts over a wider pH range than ammonium groups. Guanidinium ions form characteristic pairs of zwitterionic hydrogen bonds with carboxylate anions. This type of binding, which combines electrostatic interactions and hydrogen bonded structural organization, can lead to enhanced binding strength. Additionally, the combination of electrostatic and ionic hydrogen bonding ability can enable such guanidinium moiety-containing polymer compositions to be more selective anion receptors for carboxylate anions such as bile acid salts. Since increased binding strength and selectivity is indicative of increased efficacy, the guanidinium moiety-containing polymer compositions of the invention represent an improvement over certain known bile acid sequestrants.

DETAILED DESCRIPTION OF THE INVENTION

The features and other details of the invention will now be more particularly described and pointed out below as well as in the claims. It will be understood that the particular embodiments of the invention are shown by way of illustration and not as limitations of the invention. The principle features of this invention can be employed in various embodiments without departing from the scope of the invention.

The present invention relates to polymer compositions and to methods of using said compositions for removing bile acids from a patient. The polymer composition of the invention comprise guanidinium moiety-containing polymers and physiologically acceptable salts thereof. The precise nature of the polymeric backbone is not critical to the invention as the enhanced bile acid salt binding properties of the polymer compositions are, generally, due to the nature of the interaction of bile acid salts with the guanidinium moieties. Furthermore, additional substitution of guanidinium moiety-containing polymers with, for example, hydrophobic groups can also provide superior bile acid sequestrants.

In one aspect the guanidinium moiety-containing polymer composition comprises polymers wherein the backbone of the polymer comprises said guanidinium moiety. The backbone of these polymers comprise two or more atoms of the guanidinium group. The polymers can be made by polymerization of substituted carbodiimides such as those represented by Structural Formula (I):

wherein R can be hydrogen, a substituted or unsubstituted aliphatic group, a substituted or unsubstituted aromatic group, a hydrophobic group or a quaternary ammonium-containing group. (See, for example, Heintz, A. M., and Novak, B. M., *Polymer Preprints*, 39(2):429–430 (1998).)

Polymers of this type can comprise a repeat unit represented by Structural Formula (II):

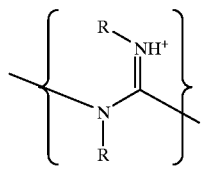

(II)

wherein R can be as described above in Structural Formula I.

In another aspect the guanidinium moiety-containing polymer compositions comprise polymers with pendant guanidinium substituents. In one embodiment, the polymer can comprise an aliphatic backbone bearing pendant guanidinium substituents as represented in Structural Formula (III). In another embodiment a terminal nitrogen atom of the guanidinium group can be contained within the backbone of the polymer, as depicted in Structural Formula (IV).

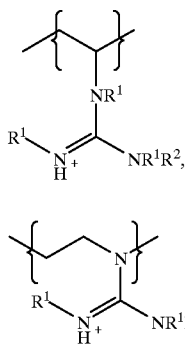

(III)

(IV)

In Structural Formulas (III) and (IV) $R^1$ and $R^2$ can each independently be hydrogen, a substituted or unsubstituted aliphatic group, a substituted or unsubstituted aromatic group, a hydrophobic group or a quaternary ammonium-containing group.

Some of the polymers of this embodiment can be prepared by reacting amine-containing polymers with guanylating agents, as described herein, to convert amines of said amine-containing polymers into quanidinium moieties.

The term "amine-containing polymer", as used herein, includes any polymer having a repeat unit characterized by an amine nitrogen atom. Thus, amine-containing polymers include polymers which have been chemically altered through chemical reactions such as hydrolysis, nucleophilic substitution and reduction to yield a polymer having a repeat unit characterized by an amine nitrogen atom, as well as polymers comprising monomers which contain an amine nitrogen or monomers which can be altered by said chemical reactions to yield a product that contains an amine nitrogen atom. An "amine nitrogen" is defined as any nitrogen atom-containing moiety which has a positive charge under the conditions present in the mammalian gastrointestinal tract. Suitable amine-containing monomers include, but are not limited to, for example, allylamine, diallylamine, diallyl methylamine, vinylamine, aminoalkyl acrylamides, aminoalkyl(meth)acrylates, ethyleneimine and vinylimidazole. Preferred repeat units are represented by Structural Formulas (V)–(XI):

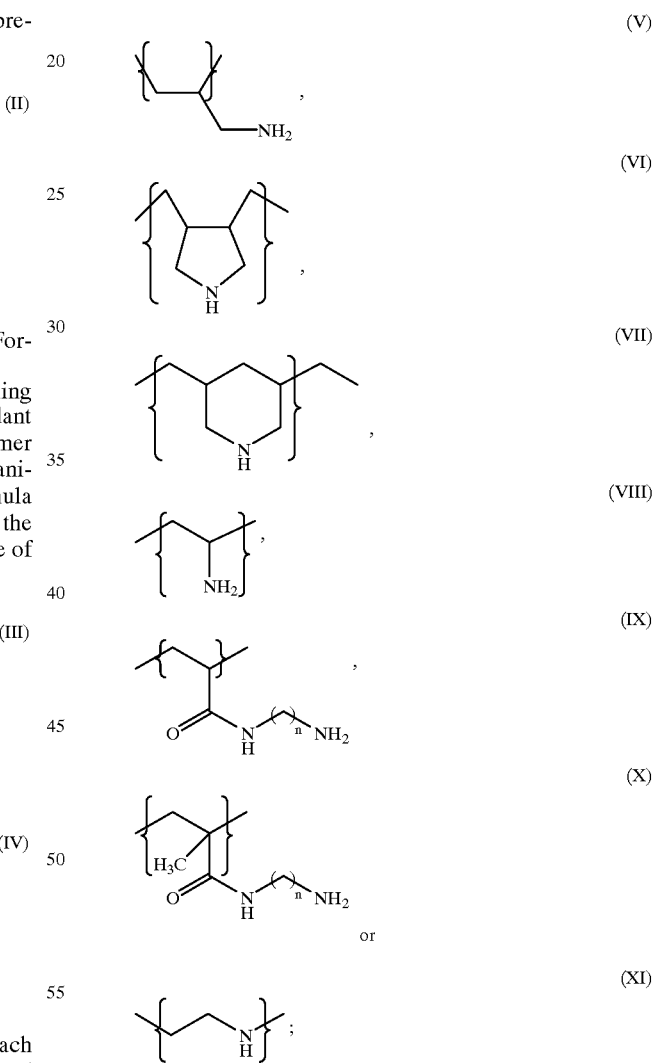

wherein n is an integer, such as an integer from zero to about twenty, preferably between about three and ten.

A "guanylating agent," as that term is employed herein, refers to a reactant that, when reacted with an amine-containing monomer or a polymer characterized by an amine-containing repeat unit of the invention, results in substitution of the amine nitrogen, converting said amine into a guanidinium moiety as shown in Scheme I.

Scheme I

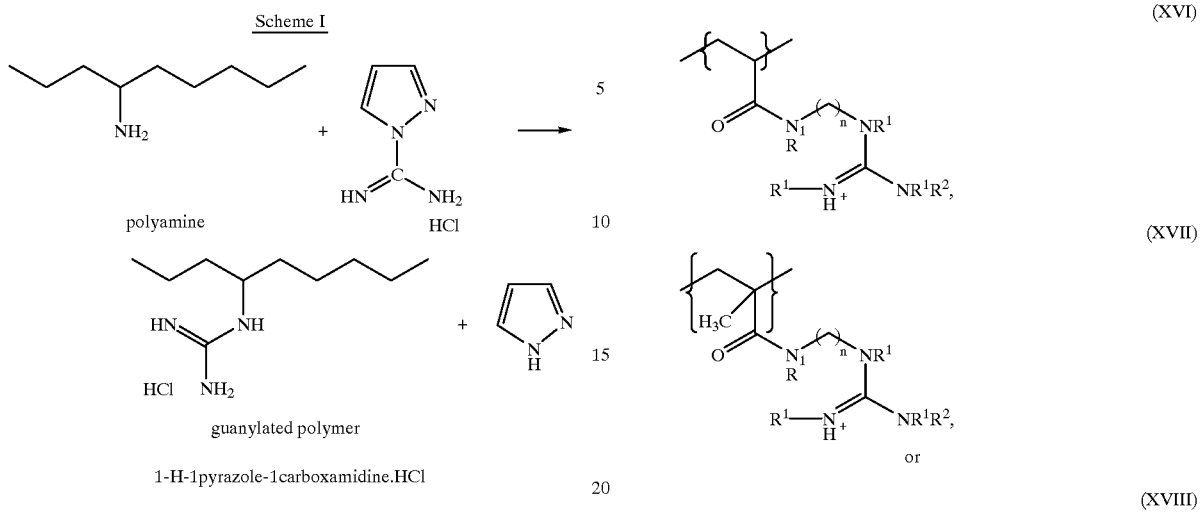

polyamine + 1-H-1pyrazole-1carboxamidine·HCl → guanylated polymer + pyrazole

For example, an amine-containing polymer comprising a repeat unit selected from those represented by Structural Formulas (V)–(XI) can be guanylated to produce a polymer comprising a repeat unit selected from those represented by Structural Formulas (XII)–(XVIII):

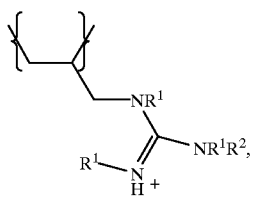

(XII)

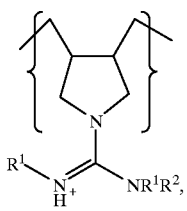

(XIII)

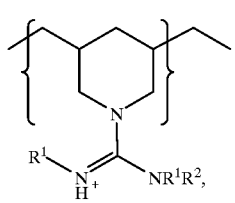

(XIV)

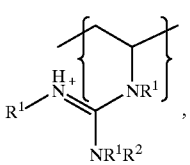

(XV)

(XVI)

(XVII)

or (XVIII)

wherein n is an integer, such as an integer from zero to about twenty, preferably between about three and ten, and $R^1$ and $R^2$ can be as defined in Structural Formulas (III) and (IV).

Guanylating agents suitable for use in the invention include, but are not limited to, thioureas, chloroformamidines, dichloroisocyanides, carbodiimides, cyanamides, compounds comprising an aminoimino group that is bonded to a suitable leaving group, for example aminoiminomethane sulfonic acids and 1-H-pyrazole-1-carboxamidine-HCl, and phosgenizum salts (see Schlama, T. et al., *J. Org. Chem.*, 62:4200 (1997)). A preferred guanylating agent is 1-H-pyrazole-1-carboxamidine-HCl.

In addition to the guanidinium substituents shown in Structural Formulas (III) and (IV) above, the polymers of the invention can comprise cyclic guanidinium substituents. In a specific embodiment, the polymers comprise a cyclic guanidinium substituent represented by Structural Formula (XIX):

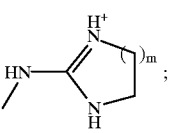

(XIX)

wherein m is an integer from one to about six.

In a preferred embodiment, the guanidinium moiety-containing polymer composition comprises a guanidinium moiety-containing polymer that is substituted by a hydrophobic group, a quaternary ammonium-containing group or combinations thereof. The substituent or substituents can be bonded to an amine nitrogen atom which is not an atom of the guanidinium moiety, to an amine nitrogen atom that is an atom of the guanidinium moiety or to a combination thereof. Preferably, the substituent or substituents are bonded to an amine nitrogen atom which is not an atom of the guanidinium moiety.

As used herein, aliphatic groups include straight chained, branched or cyclic $C_1$–$C_{24}$ hydrocarbons which are completely saturated or which contain one or more units of unsaturation. For example, suitable aliphatic groups include substituted or unsubstituted linear, branched or cyclic $C_1$–$C_{24}$ alkyl, alkenyl or alkynyl groups. Optionally, one or more of the carbon atoms in an aliphatic group can be replaced by a heteroatom such as oxygen, nitrogen or sulfur.

An "alkyl group" is a saturated aliphatic group, as defined above.

Aromatic groups include carbocyclic aromatic rings (e.g. benzyl, phenyl, etc.) and fused polycyclic aromatic ring systems (e.g. naphthyl, anthracyl, etc.). In addition, aromatic groups include heteroaryl rings (e.g. pyridine, thiophene, furan, etc.) and polycyclic aromatic ring systems in which a carbocyclic aromatic ring or heteroaryl ring is fused to one or more other rings. For example, 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl, 3-isoindolyl, and acridinyl.

Suitable substituents on an alkyl, aliphatic or aromatic group include, for example, —OH, an electron withdrawing group, a halogen (—Br, —Cl, —I and —F), —O(aliphatic, substituted aliphatic, benzyl, substituted benzyl, aromatic or substituted aromatic group), —CN, —NO$_2$, —COOH, —NH$_2$, —NH(aliphatic group, substituted aliphatic, benzyl, substituted benzyl, aromatic or substituted aromatic group), —N(aliphatic group, substituted aliphatic, benzyl, substituted benzyl, aromatic or substituted aromatic group)$_2$, —COO(aliphatic group, substituted aliphatic, benzyl, substituted benzyl, aromatic or substituted aromatic group), —CONH$_2$, —CONH(aliphatic, substituted aliphatic group, benzyl, substituted benzyl, aromatic or substituted aromatic group), —CON(aliphatic, substituted aliphatic group, benzyl, substituted benzyl, aromatic or substituted aromatic group)$_2$, —SH, —SO$_k$(aliphatic, substituted aliphatic, benzyl, substituted benzyl, aromatic or substituted aromatic group) (k is 0, 1 or 2) and —NH—C(=NH)—NH$_2$. A substituted non-aromatic heterocyclic ring, benzyl group or aromatic group can also have an aliphatic or substituted aliphatic group as a substituent. A substituted alkyl or aliphatic group can also have a non-aromatic heterocyclic ring, benzyl, substituted benzyl, aromatic or substituted aromatic group as a substituent. A substituted non-aromatic heterocyclic ring can also have =O, =S, =NH or =N(aliphatic, aromatic or substituted aromatic group) as a substituent. A substituted aliphatic group or a substituted aromatic group can have more than one substituent.

A "hydrophobic group", as the term is used herein, is a chemical group which, as a separate entity, is more soluble in octanol than water. For example, the octyl group ($C_8H_{17}$) is hydrophobic because its parent alkane, octane, has greater solubility in octanol than in water. The hydrophobic group can be a saturated or unsaturated, substituted or unsubstituted hydrocarbon group. Such groups include substituted and unsubstituted, normal, branched or cyclic alkyl groups having at least about four, preferably at least about six, carbon atoms, substituted or unsubstituted arylalkyl or heteroarylalkyl groups and substituted or unsubstituted aryl or heteroaryl groups. Preferably the hydrophobic group includes an alkyl group of between about six and twenty-four carbon atoms. More preferably the hydrophobic group includes an alkyl group of between six and about fourteen carbon atoms. Suitable hydrophobic groups include, for example, n-hexyl, n-heptyl, n-octyl, n-nonyl, n-decyl, n-undecyl, n-dodecyl, n-tridecyl, n-tetradecyl, n-hexadecyl, n-octadecyl, n-eicosyl and combinations thereof. Other examples of hydrophobic groups include haloalkyl groups of at least about four, preferably about six, carbon atoms (e.g., 10-halodecyl), hydroxyalkyl groups of at least about four, preferably about six, carbon atoms (e.g., 11-hydroxyundecyl), and aralkyl groups (e.g., benzyl).

Suitable quaternary ammonium-containing groups include alkyl trialkylammoniums also referred to as ammonioalkyl groups. The term, "ammonioalkyl", as used herein, refers to an alkyl group which is substituted by a nitrogen bearing three additional substituents. Thus, the nitrogen atom is an ammonium nitrogen atom which bears an alkylene substituent, which links the ammonium nitrogen atom to the nitrogen atom of the amine-containing polymer, and three additional terminal alkyl substituents having from about one to twenty-four carbon atoms. A "terminal substituent" of the quaternary ammonium, as the term is employed herein, is any one of the three substituents on the quaternary ammonium nitrogen which is not the carbon chain linking the amine of the polymer and the amine of the quaternary ammonium center.

An ammonioalkyl group will further include a negatively charged counterion, such as a conjugate base of a pharmaceutically acceptable acid. Suitable counterions include, for example, Cl$^-$, Br$^-$, CH$_3$SO$^{3\,-}$, HSO$^{4-}$, SO$_4^{2-}$, HCO$^{3-}$, CO$_3^{2-}$, acetate, citrate, lactate, succinate, propionate, butyrate, ascorbate, maleate, folate, an amino acid derivative and a nucleotide.

Preferred ammonioalkyl groups can have the general formula:

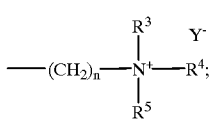

(XX)

wherein R$^3$, R$^4$ and R$^5$ independently can be a normal or branched, substituted or unsubstituted alkyl group having about one to twenty-four carbon atoms;

n is an integer, for example, n can be from three to about twenty; and,

Y is a negatively charged counterion.

The alkyl group which provides the alkylene linking group between the amine of the amine-containing polymer and the ammonium nitrogen of the alkyl trialkylammonium group can be three to about twenty carbon atoms in length. Examples of preferred alkylene linking groups are propylene, butylene, pentylene, hexylene, octylene and decylene groups. Examples of suitable quaternary ammonium-containing groups include, but are not limited to:

3-(trimethylammonio)propyl;

4-(trimethylammonio)butyl;

5-(trimethylammonio)pentyl;

6-(trimethylammonio)hexyl;

8-(trimethylammonio)octyl;

10-(trimethylammonio)decyl;

12-(trimethylammonio)dodecyl and combinations thereof. A preferred quaternary ammonium-containing group is a 6-(trimethylammonio)hexyl group.

Alternatively, a quaternary ammonium-containing group comprises one or more substituents (i.e., either a terminal substituent or the alkylene linking group and combinations thereof) which are hydrophobic as defined hereinabove. For example, the quaternary ammonium nitrogen or ammonium nitrogen of the quaternary ammonium-containing group is bonded to the amine of the polymer by an alkylene linking group having six or more carbon atoms. In a particular embodiment the quaternary ammonium-containing group is represented by Structural Formula (XX) wherein $R^3$ and $R^4$ are dodecyl groups, $R^5$ is a methyl group, n is 3 and Y is Br$^-$.

Particular examples of quaternary ammonium-containing groups containing hydrophobic substituents include, for example:

4-(dioctylmethylammonio)butyl;
3-(dodecyldimethylammonio)propyl;
3-(octyldimethylammonio)propyl;
3-(decyldimethylammonio)propyl;
6-(dimethyldecylammonio)hexyl;
6-(decyldimethylammonio)hexyl;
3-(tridecylammonio)propyl;
3-(dodecyldimethylammonio)propyl;
6-(dodecyldimethylammonio)hexyl;
4-(dodecyldimethylammonio)butyl;
3-(octadecyldimethylammonio)propyl;
3-(hexyldimethylammonio)propyl;
3-(methyldioctylammonio)propyl;
3-(didecylmethylammonio)propyl;
3-(heptyldimethylammonio)propyl;
3-(dimethylnonylammonio)propyl;
6-(dimethylundecylammonio)hexyl;
4-(heptyldimethylammonio)butyl;
4-(dioctylmethylammonio)butyl;
6-(octyldimethylammonio)hexyl;
12-(decyldimethylammonio)dodecyl;
3-(dimethylundecylammnio)propyl; and
3-(tetradecyldimethylammonio)propyl.

The polymer composition of the invention can be formed, for example, by the synthesis of polymerizable olefin derivatives bearing guanidinium functions and their subsequent free radical polymerization. Preferably, the polymers are formed by reacting an amine-containing polymer, which can be linear or crosslinked, with a suitable guanylating agent or by polymerizing guanylated monomers.

In one embodiment, the polymer composition comprises a guanidinium moiety-containing polymer that is substituted by a hydrophobic group, a quaternary ammonium-containing group, or a combination thereof. Polymers of this type can be formed, for example, by the polymerization of a carbodiimide represented by Structural Formula (I), wherein R is a hydrophobic group, a quaternary ammonium-containing group, or a combination thereof. Preferably, the guanidinium moiety-containing polymers which are substituted by a hydrophobic group, a quaternary ammonium-containing group or combinations thereof, are formed, for example, by reacting an amine-containing polymer, which can be linear or crosslinked, with a suitable alkylating agent to yield an alkylated polymer. The alkylated polymer is then reacted with a guanylating agent to yield the guanidinium moiety-containing polymer which is substituted by a hydrophobic group or a quaternary ammonium-containing group. Alternatively, the polymer compositions can be formed by alkylating a monomer and then copolymerizing said alkylated monomer, or combination of alkylated monomers, with a guanylated monomer.

An "alkylating agent," as that term is employed herein, refers to a reactant that, when reacted with an amine-containing monomer or a polymer characterized by an amine-containing repeat unit, results in the covalent bonding of a substituent (e.g., a hydrophobic group or quaternary ammonium-containing group as described herein) to one or more of the amine nitrogen atoms of the monomer or polymer. It is to be understood that under certain conditions, hydroxyl groups contained in the polymer compositions can also react with alkylating agents. Further, when multiple substituents are employed, they can be bonded to the same and/or different amine nitrogen atoms.

Suitable alkylating agents are compounds comprising an alkyl group or alkyl derivative, having at least about four, preferably about six, carbon atoms, which is bonded to a leaving group such as a halo (e.g., chloro, bromo or iodo), tosylate, mesylate or epoxy group.

Examples of suitable alkylating agents which provide a hydrophobic group include alkyl halides (e.g., chlorides or bromides) such as n-hexyl halide, n-heptyl halide, n-octyl halide, n-nonyl halide, n-decyl halide, n-undecyl halide, n-dodecyl halide, n-tetradecyl halide, n-octadecyl halide, and combinations thereof. Other examples include: a dihaloalkane (e.g., a 1,10-dihalodecane); a hydroxyalkyl halide (e.g., an 11-halo-1-undecanol); an aralkyl halide (e.g., a benzyl halide); an alkyl epoxy ammonium salt(e.g., glycidylpropyl-trimethylammonium salts) and epoxyalkylamides (e.g., N-(2,3-epoxypropyl) butyramide or N-(2,3-epoxypropyl) hexanamide). Preferred halogen components of the alkyl halides are bromine and chlorine. Particularly preferred alkylating agents which, when reacted with the polymer composition, will result in an amine polymer reaction product that includes a hydrophobic substituent, include, for example 1-bromodecane and 1-chlorodecane.

Examples of suitable alkylating agents which can provide a quaternary ammonium-containing moiety have the general formula:

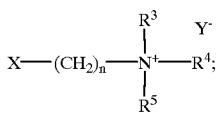

(XXI)

wherein $R^3$, $R^4$, and $R^5$ represent an alkyl group, wherein each independently, is a normal or branched, substituted or unsubstituted alkyl group having about one to about twenty-four carbon atoms, n is an integer, for example, n can have a value of three or more, X is a leaving group as described hereinabove, and Y is a negatively charged counterion.

When at least one of the three terminal substituents of the quaternary ammonium alkylating agent is a hydrophobic alkyl group having from about four to about twenty-four carbons, the alkylating agent therefore provides both a hydrophobic moiety and a quaternary ammonium-containing moiety. The alkylene group in this instance is three or more carbon atoms in length.

Particular examples of quaternary ammonium compounds suitable as alkylating agents include the following:

(4-bromobutyl)dioctylmethylammonium bromide;
(3-bromopropyl)dodecyldimethylammonium bromide;

(3-chloropropyl)dodecyldimethylammonium bromide;
(3-chloropropyl)decyldimethylammonium bromide;
(5-tosylpentyl)dodecyldimethylammonium bromide;
(6-bromohexyl)dimethyldecylammonium bromide
(12-bromododecyl)decyldimethylammonium bromide;
(3-bromopropyl)tridecylammonium bromide;
(3-bromopropyl)dodecyldimethylammonium bromide;
(6-bromohexyl)dodecyldimethylammonium bromide;
(4-chlorobutyl)dodecyldimethylammonium bromide;
(3-chloropropyl)octadecyldimethylammonium bromide;
(3-bromopropyl)octyldimethylammonium bromide;
(3-iodobutyl)dioctylmethylammonium bromide;
(4-iodobutyl)dioctylmethylammonium bromide;
(2,3-epoxy propyl)decyldimethylammonium bromide; and
(3-bromohexyl)docosyldimethyammonium bromide Examples of suitable alkyl trimethylammonium alkylating agents include alkyl halide trimethylammonium salts, such as:

(4-halobutyl)trimethylammonium salt;
(5-halopentyl)trimethylammonium salt;
(6-halohexyl)trimethylammonium salt;
(7-haloheptyl)trimethylammonium salt;
(8-halooctyl)trimethylammonium salt;
(9-halononyl)trimethylammonium salt;
(10-halodecyl) trimethylammonium salt;
(11-haloundecyl)trimethylammonium salt;
(12-halododecyl)trimethylammonium salt; and combinations thereof. A particularly preferred quaternary ammonium-containing alkylating agent is (6-bromohexyl)-trimethylammonium bromide.

Guanylation and alkylation of the amine-containing polymer or monomer can be achieved by reacting the free base form of the polymer or monomer with a guanylating or alkylating agent, or combinations thereof, under conditions which are apparent to those of skill in the art. For example, the free base form of a polymer composition is combined with a guanylating or alkylating agent in a reaction solvent. The reaction mixture is stirred at a temperature ranging from room temperature to about 75° C. The reaction period is typically from about three to eighteen hours. The reaction product, a guanylated or alkylated polymer composition, is then recovered by filtration, washing and drying. Suitable reaction solvents include methanol, ethanol, isopropanol, acetonitrile, water and mixtures thereof.

The amount of guanylating and alkylating agents used will depend on the specific polymer composition desired. For example, to produce a polymer composition comprising a guanidinium moiety-containing polymer, the total amount of guanylating agent combined with the polymer composition is generally sufficient to cause reaction of the guanylating agent with about 10 to 100% of amine groups on the polymer composition. For example, the amount of guanylating agent can be sufficient to react with between 50 and 100% or 75 and 100% of amine groups on the polymer. To produce a polymer composition comprising a guanidinium moiety-containing polymer that is substituted by a hydrophobic group, a quaternary ammonium-containing group or combinations thereof. The hydrophobic and/or quaternary ammonium-containing group can be introduced by partial alkylation of the polymer composition prior to guanylation. For example, the polymer composition can be reacted with an amount of alkylating agent or agents sufficient to alkylate a portion of the amine groups on the polymer composition. The resulting alkylated polymer composition can then be reacted with an amount of a guanylating agent that is sufficient to guanylate the remaining amine groups on the polymer composition to the desired degree.

Polymers and monomers bearing pendant guanidinium derivatives, such as, cyclic guanidinium substituents can be prepared by following the procedures described herein and the analogous procedures adopted for the synthesis of low molecular weight guanidinium derivatives.

As described above, alkylation and/or guanylation can be performed prior to and/or subsequent to polymerization. Polymerization can be accomplished using techniques known in the art of polymer synthesis. (See, for example, Shalaby et al., ed., Water-Soluble Polymers, American Chemical Society, Washington, D.C. [1991]). The appropriate monomers can be polymerized by methods known in the art, for example, via a free radical addition process. In this case the polymerization mixture includes a free-radical initiator. Suitable free-radical initiators include azobis (isobutyronitrile), azobis(4-cyanovaleric acid), azobis (amidinopropane dihydrochloride), potassium persulfate, ammonium persulfate, and potassium hydrogen persulfate. Other suitable initiators include ionizing radiation and ultraviolet light. The free radical initiator is preferably present in the reaction mixture in an amount ranging from about 0.1 mole percent to about 5 mole percent relative to the monomer.

The polymer composition can be linear or crosslinked. Crosslinking can be performed by reacting the polymer with one or more multifunctional crosslinking agents. The term "multifunctional crosslinking agent", as used herein, refers to a molecule having two or more reactive groups, such as electrophilic groups, which react with amine groups to form a covalent bond. Crosslinking in this case can occur, for example, via nucleophilic attack of the polymer amino groups on the electrophilic groups. This results in the formation of a bridging unit which links two or more amino nitrogen atoms from different polymer strands. Multifunctional crosslinking agents of this type include compounds having two or more groups including, for example, acyl chloride, epoxide, and alkyl-X, wherein X is a suitable leaving group, such as a halo, tosyl or mesyl group. Examples of such compounds include, but are not limited to, epichlorohydrin, succinyl dichloride, acryloyl chloride, butanedioldiglycidyl ether, ethanedioldiglycidyl ether, pyromellitic dianhydride, and dihaloalkanes. A particularly preferred multifunctional crosslinking agent is epichlorohydrin.

The polymer composition can also be crosslinked by including a multifunctional co-monomer as the crosslinking agent in the reaction mixture. A multifunctional co-monomer can be incorporated into two or more growing polymer chains, thereby crosslinking the chains. Suitable multifunctional co-monomers include, but are not limited to, diacrylates, triacrylates, and tetraacrylates, dimethacrylates, diacrylamides, diallylacrylamides, and dimethacrylamides. Specific examples include ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), pentaerythritol tetraacrylate, trimethylolpropane triacrylate, bisphenol A dimethacrylate, and bisphenol A diacrylate. Other suitable multifunctional monomers include polyvinylarenes, such as divinylbenzene.

The amount of multifunctional co-monomer is typically between 0.5 and 25 weight %, based upon the combined weight of said multifunctional co-monomer and monomer, with 0.5–20%, or 1–10%, being preferred. Typically, the amount of multifunctional crosslinking agent that is reacted with the polymer composition is sufficient to cause between about 0.5 and twenty percent of the amines to react with said agent. In a preferred embodiment, between about 5 and 15 percent of the amine groups react with said agent. For example, the amount of multifunctional crosslinking agent that is reacted with the polymer composition can be sufficient to cause between about two and six percent of the amines to react with said agent. It is to be understood that under certain conditions, hydroxyl groups contained in the polymer compositions can also react with the crosslinking agent.

Crosslinking of the polymer composition can be achieved by reacting the polymer with a suitable multifunctional crosslinking agent in an aqueous caustic solution at about 25° C. for a period of time of about eighteen hours to thereby form a gel. The gel is then combined with water and blended to form a particulate solid. The particulate solid can then be washed with water and dried under suitable conditions, such as a temperature of about 50° C. for a period of time of about eighteen hours.

The polymer composition can be crosslinked prior, concurrent or subsequent to alkylation and/or guanylation.

In another embodiment, the pendant guanidinium groups are bonded to the polymer backbone through an amide bond. These polymers can be prepared by reacting a monomer or polymer which comprises a functional group derived from a carboxylic acid (e.g., acyl halide, ester or acid anhydride) with an amino(alkyl)guanidine compound, such as (4-aminobutyl)guanidine sulfate or aminoguanidine bicarbonate. For example, the N-hydroxysuccinimidyl ester of acrylic acid, NHS-acrylate, can be prepared and polymerized as described herein. The resulting poly(NHS-acrylate) can be combined with (4-aminobutyl)guanidine sulfate in an aqueous caustic solution and maintained at a temperature of about 25° C. for a period of time of about four days to yield a guanidinium moiety-containing polymer of the invention.

The polymer compositions of the invention are non-toxic and stable when ingested by a mammal. By "non-toxic" it is meant that when ingested in therapeutically effective amounts neither the polymers themselves nor any ions released into the body upon ion exchange are harmful. By "stable" it is meant that when ingested in therapeutically effective amounts the polymer compositions do not dissolve or otherwise decompose, in vivo, to form potentially harmful by-products, and remain substantially intact so that they can transport material out of the body.

The polymer composition of the invention can include copolymers comprising a guanidinium moiety-containing monomer (e.g., a guanylated amine-containing monomer) and one or more other monomers. These additional monomers can included other guanidinium moiety-containing monomers, amine-containing monomers and multifunctional co-monomers, such as those described above, for example. In addition, a copolymer can further comprise non-amine-containing monomers, for example, allyl alcohol, vinyl alcohol, ethylene oxide, propylene oxide, substituted and unsubstituted acrylates and methacrylates, such as hydroxyethylacrylate, hydroxyethylmethacrylate, hydroxypropylacrylate, hydroxypropylmethacrylate, poly(propyleneglycol) monomethacrylate, poly(ethyleneglycol) monomethacrylate, acrylic acid, carbon monoxide, and sulfur dioxide. In copolymers comprising sulfur dioxide, the polymer backbone includes —SO$_2$— units between pairs of amine-containing monomers or repeat units.

Copolymers of the invention can be formed by the methods described above, for example, an amine-containing monomer, such as vinylamine, diallylamine or ethyleneimine, can be polymerized with one or more additional monomers. The resulting copolymer can then be crosslinked, alkylated and guanylated as described above to produce the polymer composition of the invention.

The polymer composition of the invention are of sufficient size or are sufficiently crosslinked so as to minimize or prevent their absorption from the mammalian gastrointestinal tract. Thus, linear polymers of the invention are of a molecular weight greater than about 2,000 Daltons. Crosslinked polymers, however are not generally characterized by molecular weight. The crosslinked polymers discussed herein are, preferably, sufficiently crosslinked to resist absorption from the mammalian gastrointestinal tract.

In a specific embodiment, the polymer compositions are characterized by a repeat unit represented by Structural Formula (XXII):

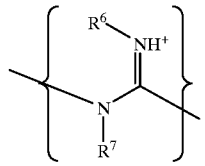

(XXII)

wherein $R^6$ and $R^7$ are each independently hydrogen, a hydrophobic group or a quaternary ammonium-containing group, with the proviso that $R^6$ and $R^7$ are not both hydrogen. These polymer compositions can be formed by polymerization of monomers represented by Structural Formula (I) via a free radical addition process. When R in said monomer is hydrogen, the polymer can be crosslinked and alkylated as described herein to yield a polymer composition which is representative of Structural Formula (XXII).

In another embodiment, the guanidinium moiety-containing polymer composition is formed by guanylating an amine-containing polymer.

In another embodiment, the guanidinium moiety-containing polymer composition is formed by partially alkylating an amine-containing polymer as described hereinabove. The alkylated polymer composition is then guanylated as described hereinabove.

In a preferred embodiment, the guanidinium moiety-containing polymer composition is formed by crosslinking an amine-containing polymer. The crosslinked product is then guanylated.

In another preferred embodiment, the guanidinium moiety-containing polymer composition is formed by crosslinking an amine-containing polymer. The crosslinked product is then partially alkylated as described hereinabove. The crosslinked alkylated polymer composition is then guanylated as described hereinabove.

In a particularly preferred embodiment, poly(diallylamine) is crosslinked with epicholorohydrin. The crosslinked product is partially alkylated with n-decylbromide to produce crosslinked poly(n-decyldiallylamine-co-diallylamine) which is guanylated to produce the guanidinium moiety-containing polymer composition.

The invention also provides methods of use of the guanidinium moiety-containing bile acid sequestrants of the invention, namely, guanidinium moiety-containing polymer compositions. The method comprises the oral administration to a mammal of a therapeutically effective amount of a guanidinium moiety-containing bile acid sequestrant to bind bile acids, reduce blood cholesterol, treat atherosclerosis, treat hypercholesterolemia and/or reduce plasma lipid content of the mammal. Generally, a therapeutic amount of a guanidinium moiety-containing bile acid sequestrant, is an amount in a range of from about 1 mg/kg/day to about 1 g/kg/day, preferably between about 1 mg/kg/day to about 200 mg/kg/day.

In one embodiment, the method of the invention is a method for binding bile acids in a mammal, comprising the step of orally administering to the mammal a therapeutically effective amount of a guanidinium moiety-containing bile acid sequestrant.

In another embodiment, the invention is a method for reducing blood cholesterol in a mammal, comprising the step of orally administering to the mammal a therapeutically effective amount of a guanidinium moiety-containing bile acid sequestrant. In still another embodiment, the invention includes a method for treating atherosclerosis in a mammal, comprising the step of orally administering to the mammal a therapeutically effective amount of a guanidinium moiety-containing bile acid sequestrant.

In still another embodiment, the method of the invention is that of treating hypercholesterolemia in a mammal, comprising the step of administering to the mammal a therapeutically effective amount of a guanidinium moiety-containing bile acid sequestrant.

The methods described herein can comprise the administration of a polymer composition of the invention in combination with any known or later developed antihyperlipoproteinemic or cholesterol lowering agent or agents, for example, aryloxyalkanoic acid derivatives, HMG CoA reductase inhibitors, nicotinic acid derivatives, thyroid hormones and analogs and other bile acid sequestrants to bind bile acids, reduce blood cholesterol, treat atherosclerosis and/or treat hypercholesterolemia.

As used herein, the term, "therapeutically effective amount," refers to an amount which is sufficient to bind bile acids, reduce blood cholesterol, treat atherosclerosis and/or treat hypercholesterolemia.

The guanidinium moiety-containing bile acid sequestrants of the invention include salts of guanidinium moiety-containing polymers. By the term, "salt", it is meant that the protonated guanidinium moiety is associated with an exchangeable negatively charged counterion. Examples of suitable counterions include $Cl^-$, $Br^-$, $CH_3SO_3^-$, $HSO_4^-$, $SO_4^{2-}$, $HCO_3^-$, $CO_3^-$, acetate, lactate, succinate, propionate, butyrate, ascorbate, citrate, maleate, folate, an amino acid derivative, or a nucleotide. The counterions can be the same as, or different from, each other. For example, the guanidinium moiety-containing bile acid sequestrant can contain two different types of counterions, both of which are exchanged for the bile acids being removed. More than one guanidinium moiety-containing polymer, each with different associated counterions, can be administered as well.

Alternatively, the guanidinium moiety-containing bile acid sequestrant can have the capability of becoming charged upon ingestion at physiological pH. In the latter case, the charged guanidinium ions also pick up negatively charged counterions upon ingestion that can be exchanged for bile acids.

The guanidinium moiety-containing polymer of the invention can be subsequently treated or combined with other materials to form compositions for oral administration of the guanidinium moiety-containing bile acid sequestrant.

The present pharmaceutical compositions are generally prepared by known procedures using well known and readily available ingredients. In making the guanidinium moiety-containing bile acid sequestrant of the present invention, the polymer composition can be present alone, can by admixed with a carrier, diluted by a carrier, or enclosed within a carrier which can be in the form of a capsule, sachet, paper or other container. When the carrier serves as a diluent, it can be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Examples of suitable carriers, excipients, and diluents include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, and talc.

The invention will now be further and specifically described by the following examples. All parts and percentages are by weight unless otherwise specified.

EXEMPLIFICATION

Synthetic Methods

Example 1

Synthesis of Epichlorohydrin Crosslinked Polyallylamine

In a 500 mL beaker, 60 g of 50% aqueous solution of polyallylamine. HCl (obtained from Nitto-Boseki, Japan) was diluted with 90 mL of deionized water. While stirring, 8.85 g of NaOH was added, and stirring was continued for 2 hours. While stirring, 0.75 mL of epichlorohydrin was added. After the solution gelled, stirring was stopped and the reaction mixture was left at room temperature 48 hours. The gel was broken into small pieces and was stirred with 400 mL deionized water for 40 minutes and filtered. This process was repeated two more times, and the polymer was dried at 60° C., yielding 26 g of the polymer as a light yellow solid.

Example 2

Synthesis of Epichlorohydrin Crosslinked Polyvinylamine

In a 500 mL beaker, 73 g of 29.6% aqueous solution of polyvinylamine (obtained from Air Products Corp.) was diluted with 70 mL of deionized water. While stirring, 1.7 mL of epichlorohydrin was added to this aqueous polymer solution. After polymer solution gelled, stirring was discontinued. The reaction mixture was allowed to stand at room temperature for 48 hours. The polymer gel was broken into smaller pieces and was stirred in 1 L deionized water for 30 minutes. The polymer was filtered, and this washing process was repeated two more times. After filtration, the polymer was dried at 60° C., yielding 28 g of the polymer as a light yellow solid.

Example 3

Synthesis of Epichlorohydrin Crosslinked Polydiallylamine

Diallylamine.HCl monomer was obtained by treating diallylamine with conc.HCl. The resulting monomer was polymerized as a 50% aqueous solution using 2,2'-azobis (2-amidinopropane) dihydrochloride (V-50 from Wako) as the free radical initiator. This polymer solution (60 g) was diluted with 90 mL of deionized water, and to it 4.5 g of NaOH was added and stirred for 2 hours. While stirring, 0.53 mL of epichlorohydrin was added to the polymer solution and stirring continued. The polymer solution gelled after 30 minutes and was allowed to stand at room temperature for 48 hours. After breaking into smaller pieces, the polymer was suspended in 1 L of deionized water, stirred for 30 minutes, and filtered. After repeating this process two more times, the filtered polymer was dried at 60° C., yielding 25 g of the polymer as a light yellow solid.

Example 4

Synthesis of Epichlorohydrin Crosslinked Polyallylamine Free Base

Crosslinked polyallylamine (25 g, Example 1) was suspended in 1 L of deionized water. While stirring, a 50% aqueous solution of NaOH was added dropwise while measuring the pH. When the pH reached ~12.0, addition of NaOH was stopped and stirring continued for an additional 45 minutes. The polymer was filtered and was washed thoroughly with deionized water until the pH of the washings was ~7.0. Filtration and drying of the solid mass yielded 22 g of polymer as off-white solid.

Example 5

Synthesis of Epichlorohydrin Crosslinked Polydiallylamine Free Base

Crosslinked polydiallylamine (25 g, Example 3) was suspended in 600 of deionized water. While stirring, a 50% aqueous solution of NaOH was added dropwise while measuring the pH. When the pH reached ~12.0, addition of NaOH was stopped and stirring continued for an additional 45 minutes. The polymer was filtered and was washed thoroughly with deionized water until the pH of the washings was ~7.0. Filtration and drying of the solid mass yielded 15.5 g of polymer as off-white solid.

Example 6

Guanylation of Epichlorohydrin Crosslinked Polyallylamine

Crosslinked polyallylamine free base (5 g, Example 4) was suspended in a 500 mL 3-necked round bottomed flask and was dispersed in 100 mL deionized water. While stirring, a solution of 14 g of 1-H-pyrazole-1-carboxamidine.HCl (Aldrich) and 9.3 g of sodium carbonate dissolved in 100 mL of deionized water was added to this polymer suspension. After stirring at room temperature for 24 hours, the polymer was filtered. It was dispersed in 500 mL of deionized water, stirred for 40 minutes, and filtered. This process was repeated three more times. Finally, the washed polymer was dispersed in 100 mL of deionized water, and 4 mL of conc. HCl was added. After stirring for 30 minutes, the polymer was filtered and dried at 60° C., yielding 8 g of the polymer as off-white solid.

Example 7

Guanylation of Epichlorohydrin Crosslinked Polyvinylamine

Crosslinked polyvinylamine (4.3 g, Example 2) was suspended in 125 mL of deionized water. After stirring for 30 minutes, a solution of 7.3 g of 1-H-pyrazole-1-carboxamidine.HCl (Aldrich) and 7.0 g of potassium carbonate dissolved in 60 mL of deionized water was added to this polymer suspension. The reaction mixture was stirred at room temperature for 3 hours and subsequently at 60° C. for 14 hours. After cooling to room temperature, the reaction mixture was filtered and the residue was washed with 300 mL of deionized water. The polymer particles were suspended in 250 mL of deionized water, stirred for 30 minutes, and filtered. This process was repeated three more times. The polymer was subsequently dispersed in 100 mL of deionized water, and to it was added 2 mL of conc.HCl. After stirring for 30 minutes, the slurry was filtered, and the isolated solid was dried at 60° C., yielding 6 g of the polymer as off-white solid.

Example 8

Guanylation of Epichlorohydrin Crosslinked Polydiallylamine

Crosslinked polydiallylamine free base (10 g, Example 5) was suspended in 225 mL of deionized water. After stirring for 30 minutes, a solution of 19.0 g 1-H-pyrazole-1-carboxamidine.HCl (Aldrich) and 17.5 g of potassium carbonate dissolved in 125 mL of deionized water was added to this polymer suspension. The reaction mixture was stirred at room temperature for 3 hours and subsequently at 60° C. for 16 hours. After cooling to room temperature, the reaction mixture was filtered, and the residue was washed with 500 mL of deionized water. The polymer particles were suspended in 500 mL of deionized water, stirred for 30 minutes, and filtered. This process was repeated three more times. The polymer was subsequently dispersed in 200 mL of deionized water, and 4 mL of conc.HCl was added. After stirring for 30 minutes, the slurry was filtered, and the solated solid was dried at 60° C., yielding 18.4 g of the polymer as off-white solid.

Example 9

Synthesis of Crosslinked Poly(N-decylallylamine-co-allylamine)

Crosslinked polyallylamine free base (10 g, Example 4) was suspended in 150 mL of deionized water, and a solution of 11.6 g of l-bromodecane dissolved in 50 mL of ethanol was added to the suspension. The reaction mixture was stirred at room temperature for 30 minutes and subsequently at 75° C. for 18 hours. After cooling to room temperature, the polymer was filtered and was washed with 50 mL of methanol. It was stirred with 400 mL of methanol for 30 minutes and filtered. The methanol wash was repeated one more time. Subsequently, the polymer particles were suspended in 400 mL of 2M NaCl and stirred for 40 minutes and filtered. After repeating this NaCl treatment one more time, the polymer particles were suspended in 400 mL of deionized water, stirred for 30 minutes, and filtered. After repeating this water washing process two more times, the polymer particles were dried at 60° C., yielding 16.3 g of off-white solid.

Example 10

Guanylation of Crosslinked Poly(N-decylallylamine-co-allylamine)

To a suspension Of 5 g of poly(N-decylallylamine-co-allylamine) (Example 9) in 100 ML of deionized water, a solution of 9.0 g of 1-H-pyrazole-1-carboxamidine.HCl (Aldrich) and 8.4 g of potassium carbonate dissolved in 60 mL of deionized water was added. The reaction mixture was stirred at room temperature for 6 hours and subsequently at 65° C. for 16 hours. After cooling to room temperature, the polymer was filtered and washed with 100 mL of deionized water. The polymer particles were suspended in 500 mL of deionized water, stirred for 30 minutes, and filtered. After repeating this washing process two more times, the polymer particles were suspended in 100 mL of water, and 4 mL of conc.HCl was added. The suspension was stirred for 40 minutes, filtered, and dried at 60° C., yielding 6.3 g of polymer as off-white solid.

Example 11

Synthesis of Crosslinked Poly(N-decylvinylamine-co-vinylamine)

Crosslinked polyvinylamine (5 g, Example 2) was suspended in 60 mL of methanol, and a solution of 10 g of 1-bromodecane dissolved in 50 mL of methanol was added. The reaction mixture was stirred at room temperature for 30 minutes. After adding 10 mL of deionized water, the reaction mixture was heated to 65° C. and stirred at this temperature for 24 hours. After cooling to room temperature, the polymer was filtered and was washed with 50 mL of methanol. It was stirred with 400 mL of methanol for 30 minutes and filtered. This methanol treatment was repeated one more time, and the filtered polymer was dried at 60° C., yielding 6.7 g of polymer as a light yellow solid.

Example 12

Guanylation of Crosslinked Poly(N-decylvinylamine-co-vinylamine)

To a mixture of 100 mL of methanol and 10 mL of deionized water, 5 g of poly(N-decylvinylamine-co-vinylamine)(Example 11) was added, and the suspension was stirred for 20 minutes. To this stirred suspension, a solution of 9.0 g of 1-H-pyrazole-1-carboxamidine.HCl (Aldrich) and 8.6 g of potassium carbonate dissolved in 60 mL of deionized water was added. The reaction mixture was stirred at room temperature for 5 hours and subsequently at 70° C. for 16 hours. After cooling to room temperature, the polymer was filtered and was washed with deionized water (2×200 mL), followed by methanol (2×200 mL). Subsequently, the polymer particles were suspended in 400 mL of 2M NaCl and stirred for 40 minutes and filtered. After repeating this NaCl treatment one more time, the polymer particles were suspended in 400 mL of deionized water, stirred for 30 minutes, and filtered. After repeating this water washing process two more times, the polymer particles were suspended in 100 mL of deionized water. While stirring, 5 mL of conc.HCl was added, and stirring was continued for 30 minutes. The polymer was filtered and dried at 60° C., yielding 5.9 g polymer as off-white solid.

Example 13

Synthesis of Crosslinked Poly(N-decyldiallylamine-co-diallylamine)

Crosslinked polydiallylamine (10 g, Example 3) was suspended in 150 mL of deionized water and stirred for 25 minutes. While stirring, a solution of 7.5 g of 1-bromodecane dissolved in 25 mL of ethanol was added. The reaction mixture was stirred at room temperature for 30 minutes. The suspension was subsequently heated to 75° C. After stirring for 1 hour, 1 g of 50% aqueous NaOH was added, and heating continued for 15 hours. After cooling to room temperature, the polymer was filtered and was washed with 500 mL of methanol, followed by 500 mL of deionized water. After filtration, the solid particles were stirred with 400 mL of methanol for 30 minutes and filtered. Subsequently, the polymer particles were suspended in 400 mL of 2M NaCl and stirred for 40 minutes and filtered. After repeating this NaCl treatment two more times, the polymer particles were suspended in 400 mL of deionized water, stirred for 30 minutes, and filtered. After repeating this water washing process two more times, the polymer particles were dried at 60° C., yielding 12 g of the polymer as off-white solid.

Example 14

Guanylation of Crosslinked Poly(N-decyldiallylamine-co-diallylamine)

To a suspension of 4 g of poly(N-decyldiallylamine-co-diallylamine)(Example 13) in 100 mL of deionized water, 10 mL of 5% potassium carbonate solution was added. After stirring for 20 minutes, a solution of 7.5 g of 1-H-pyrazole-1-carboxamidine.HCl (Aldrich) and 7.0 g of potassium carbonate dissolved in 50 mL of deionized water was added. The reacion mixture was stirred at room temperature for 5 hours and subsequently at 75° C. for 18 hours. After cooling to room temperature, the polymer was filtered and washed with 300 mL of methanol. The polymer particles were suspended in 400 mL of methanol, stirred for 30 minutes, and filtered. Subsequently, the polymer particles were suspended in 400 mL of deionized water, stirred for 30 minutes, and filtered. After repeating this water washing process one more time, the filtered particles were suspended in 100 mL of deionized water, and 2 mL of conc.HCl was added. The reaction mixture was stirred for 30 minutes, filtered and dried at 60° C., yielding 5 g of polymer as off-white solid.

Example 15

Synthesis of Poly(guanidinobutylacrylamide)

The first step in the synthesis of this compound was the preparation of the NHS ester, NHS-acrylate. N-Hydroxysuccinimide (NHS, 157.5 g) was dissolved in chloroform (2300 mL) in a 5L flask. The solution was cooled to 0° C. and acryloyl chloride (132 g) was added dropwise, keeping the temperature <2° C. After addition was complete, the solution was stirred for 1.5 hours, rinsed with water (1100 mL) in a separatory funnel and dried over anhydrous sodium sulfate. The solvent was removed under vacuum and a small amount of ethyl acetate was added to the residue. This mixture was poured into hexane (200 mL) with stirring. The solution was heated to reflux, adding more ethyl acetate (400 mL). The insoluble NHS was filtered off, hexane (1L) was added, the solution was heated to reflux, ethyl acetate (400 mL) was added and the solution allowed to cool to <10° C. The solid was then filtered off and dried in a vacuum oven to yield 125.9 g. A second crop of 80 g was subsequently collected by further cooling.

The next step in the synthesis was the preparation of Poly(NHS-acrylate). NHS-acrylate (28.5g), methylenebisacrylamide (1.5g) and tetrahydrofuran (500 mL) were mixed in a 1L flask and heated to 50° C. for 4.5 hours under a nitrogen atmosphere. Azobisisobutyronitrile (0.2g) was added, the solution was stirred for 1 hour, filtered to remove excess N-hydroxysuccinimide, and heated to 50° C. for 4.5 hours under a nitrogen atmosphere. The solution was then cooled and the solid was filtered off, rinsed in tetrahydrofuran, and dried in a vacuum oven to yield 16.1 g.

The poly(NHS-acrylate) (1.5 g) prepared above was suspended in water (25 mL) containing agmatine (1.5 g) which had been adjusted to pH 9 with solid NaOH. The solution was stirred for 4 days, after which time the pH had dropped to 6.3. Water was added to a total of 500 mL, the solution was stirred for 30 minutes, and the solid was filtered off. The solid was rinsed twice in water, twice in isopropanol, and dried in a vacuum oven to yield 0.45 g.

Example 16

Synthesis of Poly(guanidinobutylmethacrylamide)

The first step in the synthesis was preparation of poly (methacryloyl chloride). Methacryloyl chloride (20 mL) divinyl benzene (4 mL of 80% purity), AIBN (0.4g) and THF (150 mL) were stirred at 60° C. under a nitrogen atmosphere for 18 hours. The solution was cooled and the solid was filtered off, rinsed in THF, then acetone, and dried in a vacuum oven to yield 8.1 g.

Poly(methacryloyl chloride) (0.5 g), agmatine sulfate (1.0 g), triethylamine (2.5 mL), and acetone (50 mL) were stirred together for 4 days. Water (100 mL) was added and the mixture stirred for 6 hours. The solid was filtered off and washed by resuspending in water (500 mL), stirring for 30 minutes and filtering off the solid. The wash was repeated twice in water, once in methanol, and the solid was dried in a vacuum oven to yield 0.41 g.

Example 17

Synthesis of Poly(guanidinoacrylamide)

The procedure for poly(guanidinobutylacrylamide) was followed substituting aminoguanidine bicarbonate (5.0 g) for the agmatine, yielding 0.75 g.

Example 18

Synthesis of Poly (N-hexyl-N'-decyl carbodiimide)

Preparation of this polyguanidine involves the synthetic steps: synthesis of N-hexyl-N'-decyl carbodiimide monomer and polymerization of the carbodiimide monomer.

Synthesis of N-hexyl-N'-decyl carbodiimide

To 16.55 g of 1-aminodecane dissolved in 100 mL of tetrahydrofuran, was added 13.1 g of hexyl isocyanate. The reaction mixture was stirred at 65° C. under a nitrogen atmosphere for 8 hours. Subsequently the reaction mixture was left at room temperature for 14 hours during which time white precipitate was formed. After filtration the residue was recrystallized from hexane to give 23 g of a white solid.

To a suspension of 20 g of triphenylphosphene dibromide in 100 mL of benzene was added 8.9 g of triethylamine. To the resulting suspension was added 10 g of the above solid. The reaction mixture was stirred at 75° C. under a nitrogen atmosphere for 3 hours. After cooling to room temperature, the reaction mixture was filtered. The solvent was removed to give a yellowish solid. Recrystallization of the residue from hexane gave 6.3 g of N-hexyl-N'-decyl carbodiimide.

Polymerization of N-hexyl-N'-decyl carbodlimide

To 5 g of N-hexyl-N'-decyl carbodilmide dissolved in 10 mL of toluene was added 1.6 mL of 1M solution of butyl-lithium in hexane. The reaction mixture was stirred at room temperature under a nitrogen atmosphere for 24 hours. The solution was subsequently poured into 100 mL of methanol and stirred for 15 minutes. The solvent was removed and the residue was redissolved in 10 mL of tetrahydrofuran. The resulting solution was added dropwise into 100 mL of methanol containing 10 ml of concentrated hydrochloric acid. After stirring for 3 hours the solvent was removed. The residue was dried under vacuum to give 3 g of an off white solid.

In Vivo Methods

The in vivo bile acid sequestration properties of polymers prepared according to the invention have been evaluated using hamsters in the animal model. The results suggest that the guanidinium polymers of the invention are highly potent bile acid sequestrants.

Example 19

Determination of Bile Acid Excreted

After a week of acclimation to our facility, the animals were transferred to special cages that separate urine and feces. They were given only water for a 24 hour period in order to synchronize their urge for food as a group. Following the 24 hour fast, they were presented a casein-based purified feed with 10% fat added plus a predetermined amount of the drug. The food was presented for a 72 hour period. Fecal material was collected for 63 hours, from the 9th to the 72nd hour. We were able to detect the point at which the animals began excreting the drug-containing diet due to the contrast in color (dark brown to white) in the two feeds. The fecal material was then freeze-dried to eliminate water weight from the material. It was then pulverized with an amalgamator to a uniform powder, and 1 g was placed in the extraction cell. A solution of 80% methanol 100 mMol NaOH was used as the extraction solvent since it is a solvent most bile acids are sufficiently soluble in and is basic enough to hydrolyze bile acid esters. The esters commonly occur in the feces and become difficult to extract if not hydrolyzed. The extraction was accelerated by holding the sample and solvent at 100° C. and 1500 psi. 0.25 mL of the extract was evaporated and reconstituted in bovine calf serum. The sample was then analyzed like a standard serum sample, enzymatically, for bile acid concentration. The concentration was multiplied by four times the volume of extract and expressed as the concentration per gram of feces. The results are presented in Table 1.

TABLE 1

In Vivo Bile Acid Sequestration Results

| Polymer composition | Dose (wt % in feed) | % Bile Acid Excreted above Control |
|---|---|---|
| Example 8 | 0.1 | 63 |
| Example 8 | 0.2 | 322 |
| Example 14 | 0.1 | 90 |
| Example 7 | 0.2 | 30 |
| Example 12 | 0.2 | 127 |
| Colestipol | 0.3 | 94 |
| Cholestyramine | 0.3 | 125 |

While this invention has been particularly shown and described with references to preferred embodiments thereof, it will be understood by those skilled in the art that various changes in form and details may be made therein without

What is claimed is:

1. A method for removing bile acids from a patient comprising administering to said patient a therapeutically effective amount of a guanidinium moiety-containing polymer composition, wherein said polymer comprises a repeat unit having an aliphatic backbone characterized in that at least 10 molar percent of the repeat units bear pendant guanidinium substituents.

2. The method of claim 1 wherein said polymer further comprises nitrogen atoms which are substituted by a quaternary ammonium-containing group, a hydrophobic group or combinations thereof.

3. The method of claim 2 wherein said quaternary ammonium-containing group is represented by the following structural formula:

$$-(CH_2)_n-\overset{R^3}{\underset{R^5}{N^+}}-R^4; \quad Y^-$$

wherein, $R^3$, $R^4$ and $R^5$ are independently substituted or unsubstituted, normal or branched alkyl groups comprising about one to twenty-four carbon atoms;

n is an integer from one to about twenty; and

Y is a negatively-charged counterion.

4. The method of claim 3 wherein:

$R^3$, $R^4$ and $R^5$ are methyl groups, and n is an integer from about three to twelve.

5. The method of claim 4 wherein n is six.
6. The method of claim 5 wherein n is eight.
7. The method of claim 6 wherein n is ten.

8. The method of claim 3 wherein at least one of $R^3$, $R^4$ and $R^5$ is a hydrophobic alkyl group having from four to about twenty-four carbon atoms, the remainder of which each, independently, have from one to twenty-four carbon atoms.

9. The method of claim 3 wherein at least two of $R^3$, $R^4$ and $R^5$ are hydrophobic alkyl groups having from four to about twenty-four carbon atoms, the remainder having from one to twenty-four carbon atoms.

10. The method of claim 3 wherein all three of $R^3$, $R^4$ and $R^5$ are hydrophobic alkyl groups having from four to about twenty-four carbon atoms.

11. The method of claim 2 wherein said hydrophobic group is a substituted or unsubstituted, normal, branched or cyclic alkyl group comprising four to about twenty-four carbon atoms.

12. The method of claim 11 wherein said hydrophobic group comprises four to about fourteen carbon atoms.

13. The method of claim 12 wherein said hydrophobic group is an octyl or decyl group.

14. A method for removing bile acids from a patient comprising administering to said patient a therapeutically effective amount of a guanidinium moiety-containing polymer composition, wherein said polymer comprises at least 10 molar percent of a repeat unit having the following structural formula:

[structural formula showing polymer repeat unit with R-NH+ and N-R groups]

wherein each R is independently hydrogen, a substituted or unsubstituted aliphatic group, a substituted or unsubstituted aromatic group, a hydrophobic group or a quaternary ammonium-containing group.

15. The method of claim 14 wherein each R is independently hydrogen, a hydrophobic group or a quaternary ammonium-containing group.

16. The method of claim 14 wherein R is hydrogen, and the nitrogen atoms are substituted by a quaternary ammonium-containing group, a hydrophobic group or a combination thereof, after polymerization.

17. The method of claim 16 wherein said polymer is crosslinked by a multifunctional crosslinking agent.

18. The method of claim 1 wherein the pendant guanidinium substituent has a terminal nitrogen atom of the guanidinium group contained within the backbone of the polymer.

19. The method of claim 1 wherein said guanidinium substituent is a guanidinium derivative represented by:

[structural formula showing imidazoline derivative with H+, HN, and $(\quad)_m$ group]

wherein m is an integer from one to about six.

20. A method for removing bile acids from a patient comprising administering to said patient a therapeutically effective amount of a guanidinium moiety-containing polymer composition, wherein said polymer comprises at least 10 molar percent of one or more repeat units selected from:

[structural formulas showing four polymer repeat units with guanidinium groups and $R^1$, $NR^1R^2$, $NR^3$ substituents]

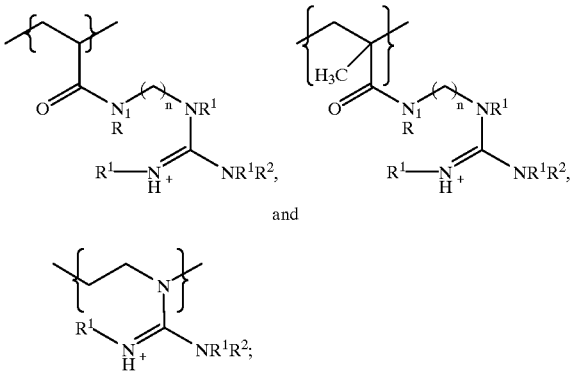

wherein n is an integer from two to about twenty; and

R¹ and R² are each independently hydrogen, a substituted or unsubstituted aliphatic group, a substituted or unsubstituted aromatic group, a hydrophobic group or a quaternary ammonium-containing group.

21. The method of claim 20 wherein said polymer further comprises one or more amine-containing monomers selected from the group consisting of allylamine, diallylamine, vinylamine, aminoalkyl acrylamides, vinylimidazole, aminoalkyl(meth)acrylates and ethyleneimine; and wherein the amine nitrogen atom of said amine-containing monomer is substituted by a quaternary ammonium-containing group, a hydrophobic group or combination thereof.

22. The method of claim 21 wherein said amine-containing monomers are substituted prior to polymerization.

23. The method of claim 22 wherein said polymer further comprises a multifunctional co-monomer.

24. The method of claim 21 wherein the amine-containing monomers are substituted after polymerization.

25. The method of claim 24 wherein said polymer is crosslinked by a multifunctional crosslinking agent; and wherein said monomers are substituted after polymerization and crosslinking.

26. The method of claim 1 wherein said polymer is a homopolymer.

27. The method of claim 1 wherein said polymer is a copolymer.

28. The method of claim 1 wherein said polymer is crosslinked.

29. The method of claim 28 wherein said polymer is a copolymer comprising a multifunctional co-monomer, said multifunctional co-monomer being present in an amount of about 0.5–25% by weight, based upon the combined weight of monomer and multifunctional co-monomer.

30. The method of claim 29 wherein said multifunctional co-monomer is present in an amount of about 1–10% by weight, based upon the combined weight of monomer and said multifunctional co-monomer.

31. The method of claim 28 wherein said polymer is crosslinked by means of a multifunctional crosslinking agent, said agent being present in an amount of about 0.5–20% of amines in the polymer.

32. The method of claim 31 wherein said multifunctional crosslinking agent is present in an amount of about 2–6% of amines in the polymer.

* * * * *

UNITED STATES PATENT AND TRADEMARK OFFICE
CERTIFICATE OF CORRECTION

PATENT NO.    : 6,294,163 B1								Page 1 of 1
DATED         : September 25, 2001
INVENTOR(S)   : Pradeep K. Dhal, Stephen R. Holmes-Farley and John S. Petersen It is certified that error appears in the above-identified patent and that said Letters Patent is hereby corrected as shown below:

Column 24,
Lines 50 through 65, delete the formula, insert the formula:

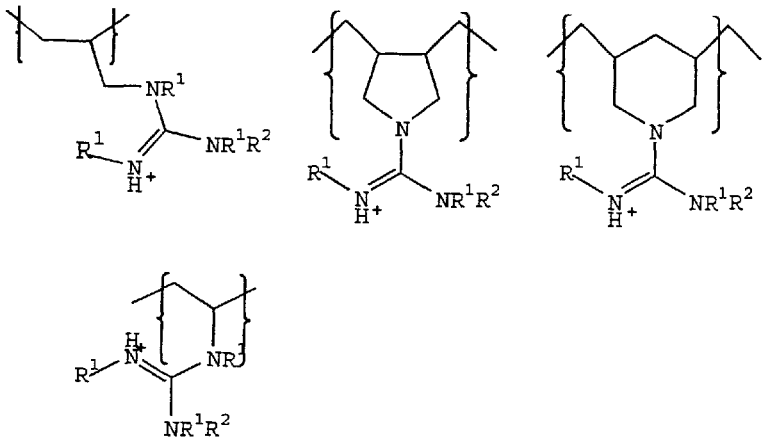

Column 25,
Line 19, delete "arc" and insert -- are --.

Signed and Sealed this

Twenty-second Day of October, 2002

*Attest:*

*Attesting Officer*

JAMES E. ROGAN
*Director of the United States Patent and Trademark Office*